US011857336B2

(12) United States Patent
Liu et al.

(10) Patent No.: US 11,857,336 B2
(45) Date of Patent: Jan. 2, 2024

(54) DETECTION AND RESPONSE TO AROUSAL ACTIVATIONS

(71) Applicant: Fitbit LLC, San Francisco, CA (US)

(72) Inventors: Man-Chi Liu, San Francisco, CA (US); Alexander Statan, Oakland, CA (US); Derrick Steven Vickers, San Francisco, CA (US); Paul Francis Stetson, Piedmont, CA (US); Elena Perez, San Francisco, CA (US); James Horng-Kuang Lin, San Jose, CA (US); Belen Lafon, San Francisco, CA (US); Lindsey Michelle Sunden, San Francisco, CA (US)

(73) Assignee: FITBIT LLC, San Francisco, CA (US)

( * ) Notice: Subject to any disclaimer, the term of this patent is extended or adjusted under 35 U.S.C. 154(b) by 204 days.

(21) Appl. No.: 17/404,051

(22) Filed: Aug. 17, 2021

(65) Prior Publication Data
US 2022/0054080 A1    Feb. 24, 2022

Related U.S. Application Data

(60) Provisional application No. 63/067,028, filed on Aug. 18, 2020.

(51) Int. Cl.
*G16H 40/63* (2018.01)
*A61B 5/16* (2006.01)
(Continued)

(52) U.S. Cl.
CPC ............ *A61B 5/486* (2013.01); *A61B 5/0205* (2013.01); *A61B 5/0245* (2013.01); *A61B 5/0531* (2013.01); *A61B 5/346* (2021.01); *A61B 5/4035* (2013.01); *A61B 5/4368* (2013.01); *A61B 5/4393* (2013.01); *A61B 5/4809* (2013.01); *A61B 5/681* (2013.01); *A61B 5/7264* (2013.01); *A61B 5/742* (2013.01); *G16H 40/60* (2018.01); *H04B 1/385* (2013.01); *H04Q 9/00* (2013.01)

(58) Field of Classification Search
None
See application file for complete search history.

(56) References Cited

U.S. PATENT DOCUMENTS

| 2011/0245633 A1 | 10/2011 | Goldberg et al. |
| 2013/0317318 A1 | 11/2013 | Tartz et al. |

(Continued)

FOREIGN PATENT DOCUMENTS

WO    WO 2019/209986    10/2019

OTHER PUBLICATIONS

International Preliminary Report on Patentability for Application No. PCT/US2021/046223, dated Mar. 2, 2023, 9 pages.
(Continued)

*Primary Examiner* — Jon Eric C Morales
(74) *Attorney, Agent, or Firm* — Dority & Manning, P.A.

(57) ABSTRACT

Arousal events can be determined for a user associated with a wearable device, such as a user wearing a wearable computing device including one or more sensors. The one or more sensors may obtain EDA information that may determine a sympathetic nervous system response of the user, which may be responsive to an arousal event or an activation. Detection of events that increase the EDA response may provide information to the user regarding arousal events and provide recommendations to the user to address the arousal events to decrease their response.

16 Claims, 12 Drawing Sheets

(51) Int. Cl.
*A61B 5/0531* (2021.01)
*A61B 5/0205* (2006.01)
*A61B 5/00* (2006.01)
*G16H 40/60* (2018.01)
*A61B 5/346* (2021.01)
*H04B 1/3827* (2015.01)
*H04Q 9/00* (2006.01)
*A61B 5/0245* (2006.01)

(56) References Cited

U.S. PATENT DOCUMENTS

2017/0173262 A1 6/2017 Veltz
2021/0233641 A1 7/2021 Sasangohar et al.

OTHER PUBLICATIONS

International Search Report and Written Opinion for Application No. PCT/US2021/046223, dated Dec. 8, 2021, 13 pages.

DETECTION AND RESPONSE TO AROUSAL ACTIVATIONS

RELATED APPLICATIONS

This application claims the benefit of U.S. Provisional Patent Application No. 63/067,028, filed on Aug. 18, 2020, which is incorporated by reference herein in its entirety.

BACKGROUND

Wearable electronic devices have gained popularity among consumers. A wearable electronic device may track a user's activities or biometric data using a variety of sensors. Data captured from these sensors can be analyzed in order to provide users with information, such as an estimation of how far they walked in a day, their heart rate, how much time they spent sleeping, and the like. However, a technical problem exists relating to users accurately and timely receiving information regarding their arousal responses due to activation of their sympathetic nervous system.

BRIEF DESCRIPTION OF THE DRAWINGS

Various embodiments in accordance with the present disclosure will be described with reference to the drawings, in which.

DETAILED DESCRIPTION

Figure 1:
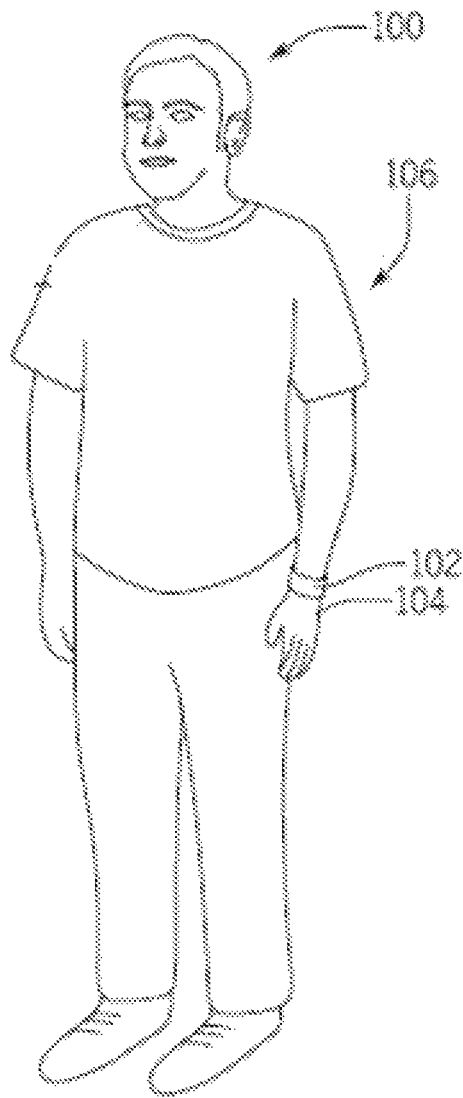
FIG. 1 illustrates an example of a user with a wearable device on an extremity, in accordance with various embodiments of the present disclosure.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Systems and methods in accordance with various embodiments of the present disclosure may utilize one or more wearable devices to detect arousal responses (e.g., activations, sympathetic nervous system responses, etc.) from electrodermal activity (EDA) and present the information to the user in order to track and/or manage their arousal responses. Embodiments may incorporate EDA measurement within one or more wearable devices, and may include information from other sensors, in order to detect changes in a user's arousal response. These changes may be compared against a baseline, that may be determined over a period of time, and once responses exceeding a threshold level are detected, the user may receive a prompt or notification providing information to the user regarding their responses to certain stimuli. In this manner, the user may use the information to track how he or she responds to different stimuli and/or to manage certain activities in his or her life. Thus, the present disclosure is directed to a technical solution/benefit to the technical problem relating to users accurately and timely receiving information regarding their arousal responses due to activation of their sympathetic nervous system.

In various embodiments, the user's sympathetic responses may be presented for visual inspection, for example, as a graph showing the user's responses over time. These responses may then be correlated with a user's activities in order to identify activities that activate the user's sympathetic nervous system, which may be detectable via the EDA measurements by measuring skin conductance responses to sweating or the like. In certain embodiments, the user may be prompted to interact with one or more wearable devices to provide data for the EDA measurements. In other embodiments, continuous EDA measurements may be obtained.

In embodiments, the user may be prompted to provide the information. By way of example, the user may receive a message on their wearable device to interact with the device in order to obtain an EDA measurement. This may be in accordance with another activity the user is undergoing, such as completing a workout, meditating, or the like. The measurements may provide information to the user regarding these activities. For example, the user's response to a workout may be different if the workout is more challenging or if the user exerted a particularly large amount of energy. Determining how the user is responding to the stimulus may be useful for developing training and/or recovery routines. In another example, during a meditation session, arousal responses may be indicative of the user losing focus or having his or her mind drift, which may enable a prompt to alert the user to facilitate changes or improvements to their meditation session. Various other activities may also be monitored and/or evaluated when using the EDA measurements, such as lie detection, stress evaluation, mental health screenings, women's health screening, and the like.

In various embodiments, EDA measurements may be obtained using a user's fingers, which may provide more accurate information than, for example, a user's arms or chest. In various embodiments, a single lead or multi-lead portion of the wearable device may provide a region where the user may position their fingers (or other body parts), measure a skin conductance, and determine a value associated with a user's arousal response associated with the sympathetic nervous system. The leads may be arranged to provide a comfortable, ergonomic position for the user. Accordingly, if the user is comfortable during the measurement or the measurement is not onerous for the user, the user is more likely to utilize the functionality of the wearable device.

Referring now to the drawings, FIG. 1 illustrates an example embodiment of a user 100 wearing a user monitoring device 102 around a wrist 104 of the user 100. The user monitoring device 102 may also be referred to herein as a wearable or a fitness tracker, and may also include devices that are worn around the chest, legs, head, or other body part, or a device to be clipped or otherwise attached onto an article of clothing worn by the user 100. The user monitoring device 102 may collectively or respectively capture data related to any one or more of caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, respiration rate and patterns, various body movements, among others. Additional data may be provided from an external source, e.g., the user may input their height, weight, age, stride, or other data in a user profile on a fitness-tracking website or application and such information may be used in combination with some of the above-described data to make certain evaluation or in determining user behaviors, such as the distance traveled or calories burned of the user. The user monitoring device 102 may also measure or calculate metrics related to the environment around the user such as barometric pressure, weather conditions, light exposure, noise exposure, and magnetic field.

In some embodiments, the user monitoring device 102 may be connected to a network directly, or via an intermediary device. For example, the user monitoring device 102 may be connected to the intermediary device via a BLUETOOTH® connection, and the intermediary device may be connected to the network via an Internet connection. In various embodiments, a user may be associated with a user account, and the user account may be associated with (i.e., signed onto) a plurality of different networked devices. In some embodiments, additional devices may provide any of the abovementioned data among other data, and/or receive the data for various processing or analysis. The additional devices may include a computer, a server, a handheld device, a temperature regulation device, or a vehicle, among others.

In the illustrated embodiment, the user monitoring device 102 may include a conductive bottom plate that is positioned against a wrist of the user 100, e.g., where the user monitoring device 102 is worn on the wrist. In such embodiments, the conductive bottom plate may serve as a first lead (e.g., first electrode) for obtaining various measurement data, such as for ECG. Additionally, in certain embodiments, one or more additional conductive areas (e.g., leads, electrodes) may be integrated into other areas of the user monitoring device 102. A location of the various additional leads may be particularly selected to enable certain types of measurements (e.g., ECG, EDA, etc.) and/or provide an ergonomic position for the user 100 while the data is collected. For example, it would be uncomfortable for the user to place a bottom of their foot on the user monitoring device 102. However, placing their opposite hand along a top of the user monitoring device 102 may be easy, and as a result, the user 100 may be more likely to utilize the features of the user monitoring device 102.

Figure 2:
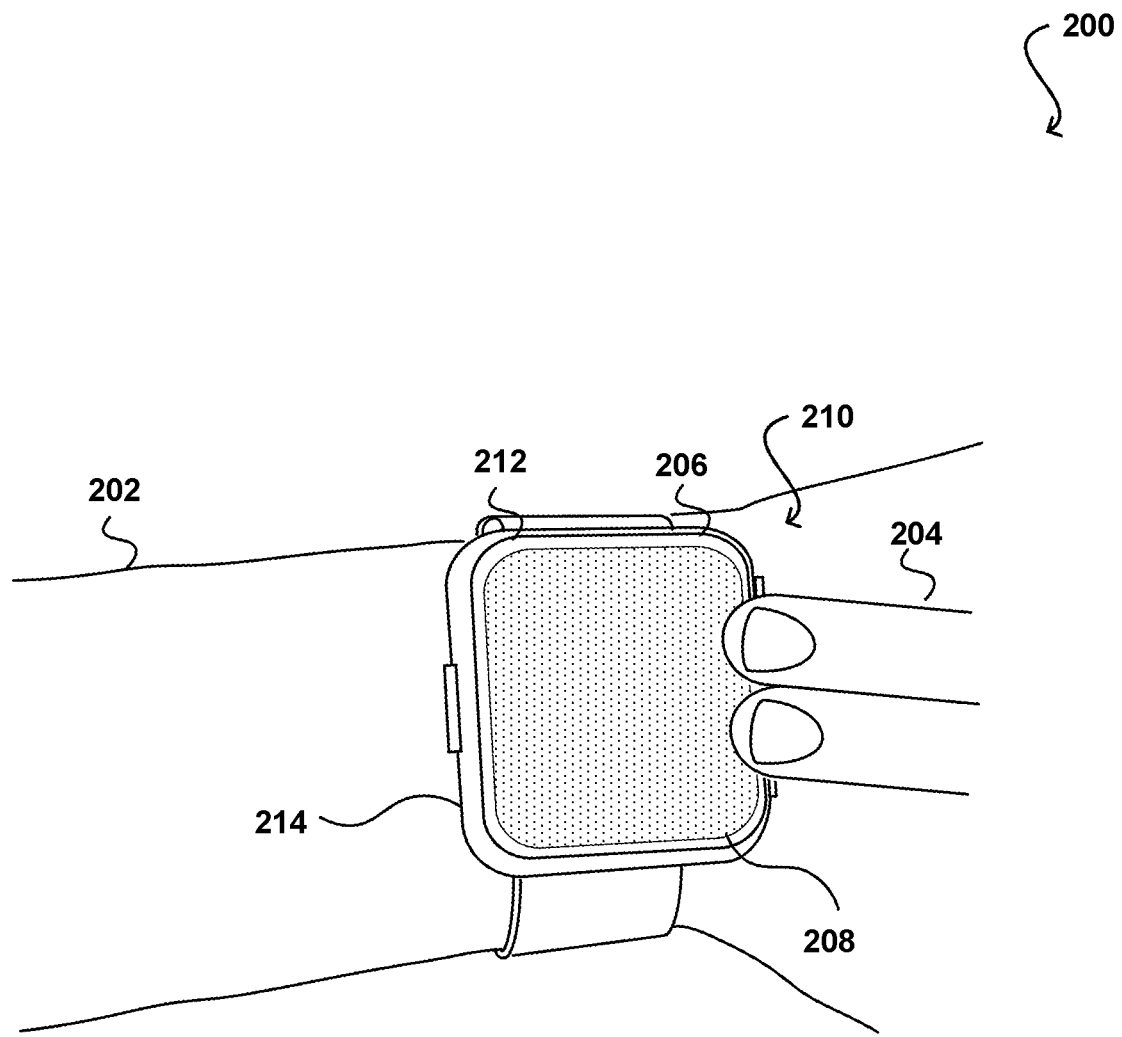
FIG. 2 illustrates an example of a user interacting with a wearable device on an extremity, in accordance with embodiments of the present disclosure.

FIG. 2 illustrates an example wearable device 200 that can be utilized in accordance with various embodiments. In this example, the wearable device 200 is a smart watch, although fitness trackers and other types of devices can be utilized as well. Further, although the wearable device 200 is shown to be worn on a user's wrist, similar to the example of FIG. 1, there can be other types of devices worn on, or proximate to, other portions of a user's body as well, such as on a finger, in an ear, around a chest, etc. For many of these devices there will be at least some amount of wireless connectivity, enabling data transfer between a networked device or computing device and the wearable device. This might take the form of a BLUETOOTH® connection enabling specified data to be synchronized between a user computing device and the wearable device, or a cellular or Wi-Fi connection enabling data to be transmitted across at least one network such as the Internet or a cellular network, among other such options.

Still referring to FIG. 2, the wearable device 200 includes a housing 210 having a display screen 208. More specifically, as shown, the housing 210 may be a multi-part component, such that the housing 210 includes a first part 212 and a second part 214. However, it should be appreciated that there may be additional parts. Moreover, in embodiments, additional components may be utilized to form one or more parts. For example, the wearable device 200 includes a conductive ring 206 that may form a portion of a bezel of the housing 210. Moreover, in an embodiment, the housing 210 may enclose one or more electronic components, which may be utilized to collect and/or analyze data, as described herein. For example, the housing 210 may enclose appropriate circuitry for ECG and/or EDA measurements. By way of example, a combination electrode may be utilized, such as the electrode described in U.S. patent application Ser. No. 16/457,363, which is hereby incorporated by reference in its entirety. The combination electrode of the '363 application may include an electrode that makes contact with the user, such as at the wrist, and a second electrode may be embedded into the bevel or surface of the wearable device, such as the configuration illustrated in U.S. patent application Ser. No. 16/935,583, which is hereby incorporated by reference in its entirety. Furthermore, as shown in the '583 application, multiple electrodes may be embedded into the wearable device face or at another location. Additionally, circuitry for performing measurements, such as ECG and/or EDA measurements, may be utilized in embodiments of the present disclosure. An example circuitry arrangement is shown in U.S. patent application Ser. No. 16/457,337, which is hereby incorporated by reference in its entirety.

In various embodiments, ergonomics and user comfort are emphasized in order to decrease the likelihood of user error and/or encourage users to utilize the functionality of the wearable device 200. For example, increasing the surface area of the electrodes may prevent shorts across both electrodes because it will be easier for the user to identify a region associated with one of the two electrodes.

As mentioned, there can be various types of functionality offered by such a wearable device, as may relate to the health of a person wearing the device. One such type of functionality relates to electrocardiography (ECG). ECG is a process that can be used to determine and/or track the activity of the heart of a person over a period of time. In order to obtain ECG data, a conductive electrode is often brought into contact with the skin of the person to be monitored. In the example embodiment of FIG. 2, the user is wearing the wearable device 200 on his or her arm 202, and can bring one or more fingers 204 (or palm, etc.) into contact with an exposed electrode of the wearable device 200. In this example, the electrode is at least a portion of the conductive ring 206 that is part of the housing 210 around the display screen 208 of the wearable device 200, although other types and forms of electrodes can be used as well within the scope of the various embodiments. In further embodiments, the housing may also be referred to as a bezel that forms an outline around the display screen 208. The electrode can be connected to an ECG circuit that can detect small changes in electrical charge on the skin that vary with the user's heartbeat. ECG data can be monitored over time to attempt to determine irregularities in heartbeat that might indicate serious cardiac issues. Conventional ECG measurements are obtained by measuring the electrical potential of the heart over a period of time, typically corresponding to multiple cardiac cycles. By a user placing his or her fingers on the exposed electrode for a minimum period of time, during which ECG measurements are taken, an application executing on the wearable device 200 can collect and analyze the ECG data and provide feedback to the user.

As mentioned, ECG measurements are taken across opposite extremities. For example, with reference to FIG. 2, a first point may be along the arm 202 (e.g., via a conductor on the underside of the wearable device 200), and a second point at the fingers 204 of the opposite arm contacting the conductor ring 206. As a result, the signal evaluates a circuit including the heart. Because the ECG is incorporated in the wearable device 200, both electrodes that form a single lead ECG sensor are incorporated into the wearable device 200, unlike traditional methods that may utilize two or more separate sensors. In various embodiments, the electrodes are electrically isolated from the device to facilitate appropriate functionality.

A user's skin impedance may decrease the reliability of data captured for the ECG measurement. As a result, reducing skin impedance is desirable. Accordingly, increasing contact surface area for each electrode is desirable. For example, forming substantially all of the bottom face of the wearable device 200 may increase the surface area in contact with the arm 202, while increasing a size of the conductive ring 206 may also decrease skin impedance. Moreover, as noted above, in various embodiments the second electrode may include one or more plated electrodes or other conductive elements that are integrated into the display screen 208, thereby increasing the conductive surface area for the second electrode.

Additionally, to further prevent user error during electrical measurements, locations for the electrodes may be particularly selected to provide comfort for users to maintain a stationary pose. For example, measurement data may be acquired over a period of time, such as 60 seconds, or longer. Movement may disrupt the measurements, and therefore, the location of the electrodes may be selected such that the user can maintain position to acquire the data. The particularly selected locations may be selected with user comfort in mind, as well as providing flexibility to enable the user to interact with the wearable device in a variety of ways. For example, different users may have ailments that make interaction with the devices difficult (e.g., arthritis, carpal tunnel, amputations, etc.), so providing a wide variety of potential interaction methods provides a greater range of use over a wider group of users.

As noted above, embodiments of the present disclosure may include a system that includes at least two independent electrodes, electrically isolated within the wearable device 200. For example, a first electrode may utilize a bottom surface area of the wearable device 200 (not pictured in FIG. 2). The bottom surface area, or a portion thereof, may make contact with the wrist 202. As will be appreciated, the bottom surface area may have one of the largest continuous surface areas for the wearable device 200, thereby achieving a goal described above to increase surface area and reduce skin impedance. In various embodiments, the first electrode is formed from a conductive electrode material and may be electrically isolated from the remainder of the wearable device 200, for example, by incorporating insulating material into the wearable device 200, such as plastics and the like. A second electrode may utilize a top surface area, or a portion thereof, of the wearable device 200. This area may be positioned such that a user can easily access the area and intuitively interact with the area. In a variety of embodiments, the display screen 208 may occupy a large portion of the top surface area, as users may prefer large displays. Accordingly, the second electrode may be incorporated into the bezel surrounding the display screen 208, as illustrated by the conductive ring 206. However, it should be appreciated that, in various embodiments, at least a portion of the display screen 208 may be utilized as the second electrode using methods that would not occlude the display, for example, by coating the display screen 208 in a conductive material (e.g., indium tin oxide), local extension of the sensor to not occlude the display, and the like. Moreover, in various embodiments, the display screen 208 may be omitted from the wearable device 200. As a result, the top surface could be substantially identical to the bottom surface. It should be appreciated that the second electrode may further be comprised of two separate, electrically isolated electrodes. For example, in various embodiments, a portion of the conductive ring 206 may be segmented and isolated from a different portion of the ring.

As noted above, embodiments of the present disclosure may go beyond configurations that include a single top electrode and a single bottom electrode to include multiple leads along the wearable device (e.g., more than one lead on the top, more than one lead on the bottom, more than one lead on both the top and bottom). Adding an electrode to the top of the wearable device 200, as described below, increases the number of ECGs and provides additional wearer configurations for obtaining measurement information. By way of example, configurations that include two electrodes along the top of the wearable device enable multiple different positions to obtain information, such as right arm to left leg and left arm to left leg, as well as augmented limb leads (e.g., aVR, aVL, and aVF). These additional leads may enable screening of a broader range of non-rhythm based conditions, and could ergonomically work by users holding the top of the device with two thumbs and pressing the bottom of the device into their leg, as an example.

While single-lead ECG can provide accurate information with regards to beat timing (also called RR interval), which can be sufficient for diagnosing many arrhythmias, multiple leads can provide additional information to more accurately diagnose conditions which rely on ECG morphology (shape). For example, sinus tachycardia is a regular rhythm that is faster than normal, and can be diagnosed from a single lead. Several conditions can cause a deviation of the electrical axis or an abnormal R-wave amplitude, which is best observed using multiple leads. Embodiments described herein may also use multi-lead ECG to examine other morphologies, such as ST-elevation or depression. Moreover, as noted above, including at least two sensors on the top may also enable EDA measurements.

As described, embodiments of the present disclosure enable multiple different user configurations for obtaining measurements using two or more leads, such as for ECG or EDA. EDA is a measurement of skin electrical resistance or conductance, which reflects the sympathetic activation in the secretory activity of sweat glands. It has been used in psychological research to understand autonomic nervous system activity and identify acute stress events induced by physical, mental, or cognitive stimuli. The skin conductance/resistance can be measured by injecting a small current between two electrodes in contact with the skin. In many instances, EDA is measured at the fingers, palm, or feet. However, in certain embodiments, wrist measurements may also be utilized for EDA. Utilizing configurations having two electrodes at the top surface of the wearable device, EDA measurements may be obtained from users in a simple, compact, and comfortable form factor.

Figure 3:
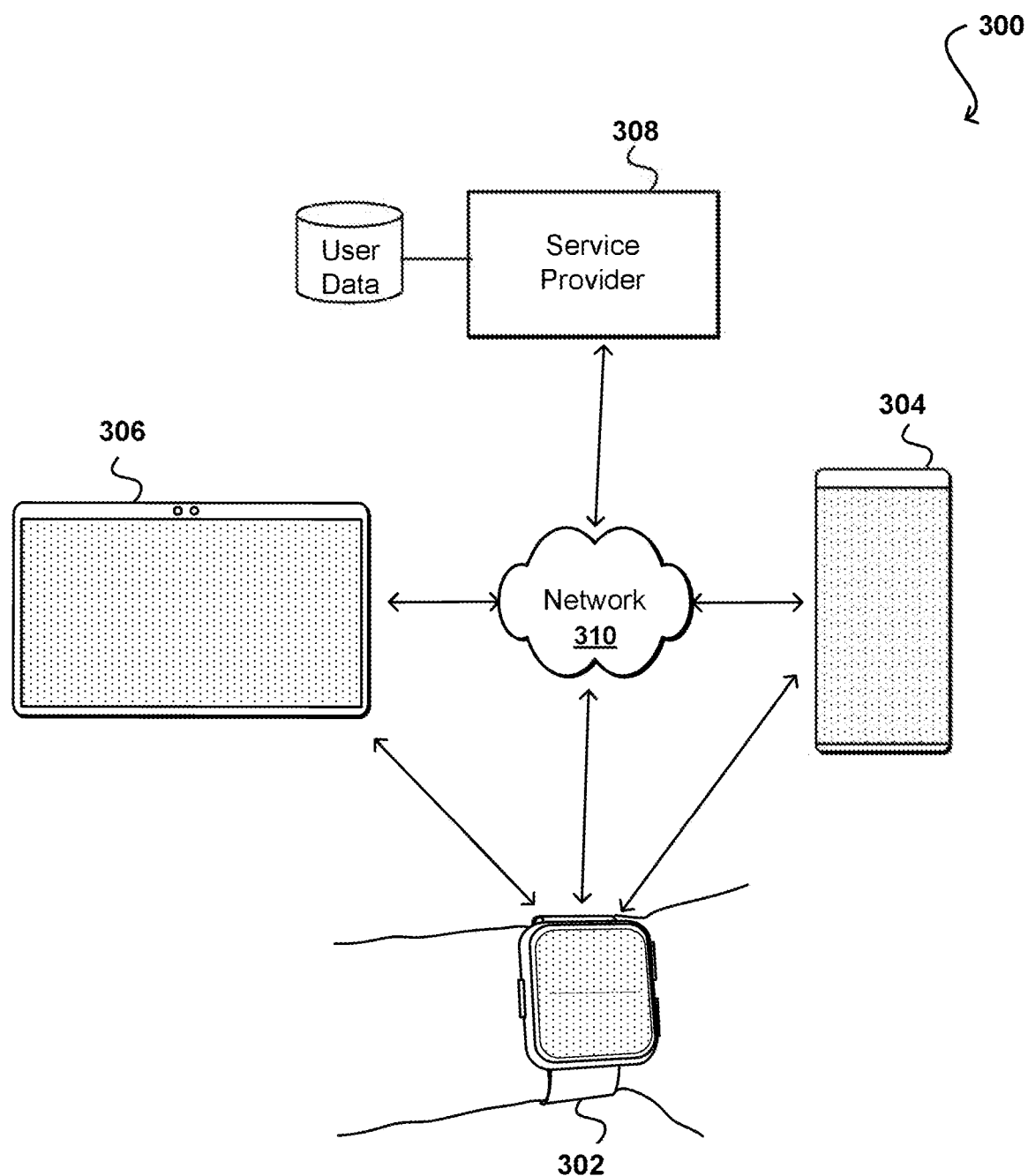
FIG. 3 illustrates an example set of devices that are able to communicate, in accordance with embodiments of the present disclosure.

FIG. 3 illustrates an example environment 300 in which aspects of various embodiments can be implemented. In this example, a person might have a number of different devices that are able to communicate using at least one wireless communication protocol. In this example, the user might have a smartwatch 302 or fitness tracker, which the user would like to be able to communicate with a smartphone 304 and a tablet computer 306. The ability to communicate with multiple devices can enable a user to obtain information from the smartwatch 302, such as heart rate data captured using a sensor on the smartwatch, using an application installed on either the smartphone 304 or the tablet 306. The user may also want the smartwatch 302 to be able to communicate with a service provider 308, or other such entity, that is able to obtain and process data from the smartwatch and provide functionality that may not otherwise be available on the smartwatch or the applications installed on the individual devices. The smartwatch may be able to communicate with the service provider 308 through at least one network 310, such as the Internet or a cellular network, or may communicate over a wireless connection such as Bluetooth® to one of the individual devices, which can then communicate over the at least one network. There may be a number of other types of, or reasons for, communications in various embodiments.

In addition to simply being able to communicate, a user may also want the devices to be able to communicate in a number of ways or with certain aspects. For example, the user may want communications between the devices to be secure, particularly where the data may include personal health data or other such communications. The device or application providers may also be required to secure this information in at least some situations. The user may want the devices to be able to communicate with each other concurrently, rather than sequentially. This may be particularly true where pairing may be required, as the user may prefer that each device be paired at most once, or that not manual pairing is required. The user may also desire the communications to be as standards-based as possible, not only so that little manual intervention is required on the part of the user but also so that the devices can communicate with as many other types of devices as possible, which is often not the case for various proprietary formats. A user may thus desire to be able to walk in a room with one device and have the device automatically be able to communicate with another target device with little to no effort on the part of the user. In various conventional approaches, a device will utilize a communication technology such as Wi-Fi to communicate with other devices using wireless local area networking (WLAN). Smaller or lower capacity devices, such as many Internet of Things (IoT) devices, instead utilize a communication technology such as Bluetooth®, and in particular Bluetooth Low Energy (BLE) that has very low power consumption.

An environment 300 such as that illustrated in FIG. 3 enables data to be captured, processed, and displayed in a number of different ways. For example, data may be captured using sensors on a smartwatch 302, but due to limited resources on that smartwatch the data may be transferred to a smart phone 304 or service provider system 308 (or a cloud resource) for processing, and results of that processing may then be presented back to that user on the smartwatch 302, smart phone 304, or another such device associated with that user, such as a tablet computer 306. In at least some embodiments, a user may also be able to provide input such as health data using an interface on any of these devices, which can then be considered when making that determination.

In at least one embodiment, data determined for a user can be used to determine state information, such as may relate to a current arousal level or state of that user. At least some of this data can be determined using sensors or components able to measure or detect aspects of a user, while other data may be manually input by that user or otherwise obtained. In at least one embodiment, an arousals determination algorithm can be utilized that takes as input a number of different inputs, where different inputs can be obtained manually, automatically, or otherwise. In at least one embodiment, such an algorithm can take various types of factors identify events or activations related to arousal or "stress" events that activate a sympathetic nervous system response.

Figure 4:
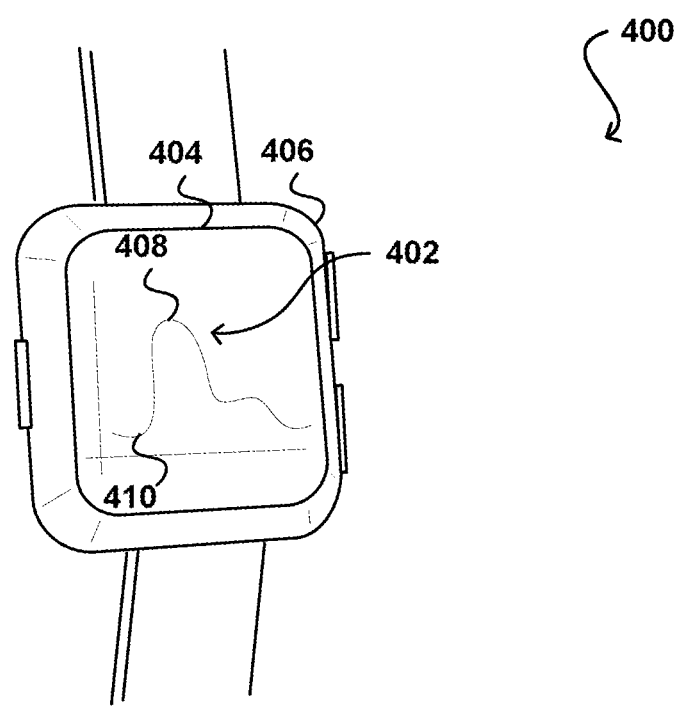
FIG. 4 illustrates an example wearable device presenting a graphical indication of arousal information, in accordance with embodiments of the present disclosure.

FIG. 4 illustrates a graphical representation 400 of an activation 402 (e.g., arousal event, arousal activation, response, stressor, etc.) provided on a display 404 of a user device 406 to the user. In this embodiment, the graphical representation 400 is provided from EDA information, which may be acquired by user device 406, as described above. In this instance, a peak detection algorithm may be utilized to determine a peak or spike 408 that is above a baseline level 410. In various embodiments, the peak or spike may be determined by evaluating a percentage difference from the baseline or may be evaluated in terms of a threshold, among other possible determinations. In various embodiments, the information may be sampled over time to determine a user's response to a stimulus and then subsequent time after the stimulus. By way of example only, different "bins" of time may be capture and averaged or normalized in order to provide the EDA information to the user. It should be appreciated that information may not be provided as a line graph, as illustrated in FIG. 4, but in various embodiments may be provided in various other graphical representations in order to provide information to the user regarding an elevated arousal level responsive to a stimulus.

In various embodiments, the information is provided to the user to illustrate their response to an event, which as noted above may be described as an arousal event, an activation, a sympathetic arousal, or the like. The information may be EDA information, which provides information regarding a skin conductance responsive to sweat or moisture on the skin. Accordingly, the illustrated embodiment may provide information to the user to inform them of a particular response to a stimulus. By way of example only, the user may notice that they have an activation or peak prior to a meeting with their boss, and as a result, the user may learn that performing a deep breathing exercise or other calming activity may be beneficial prior to the meeting.

Embodiments of the present disclosure may incorporate various information in order to generate the graphical representation 400, which may include additional information other than EDA information. For example, the user device 406 may include other sensors, which may provide context to the information. The user may have a first baseline when working and a second baseline while exercising. Accordingly, the user device 406 may be used to determine the user is exercising (e.g., elevated heart rate, set to exercise mode, GPS information, etc.) and may compare the user's response differently from when the user is resting, because the stimulus response may be known and expected while the user is exercising or doing another known strenuous activity. As will be described below, in various embodiments the user device 406 may prompt the user to provide the EDA information.

Figure 5:
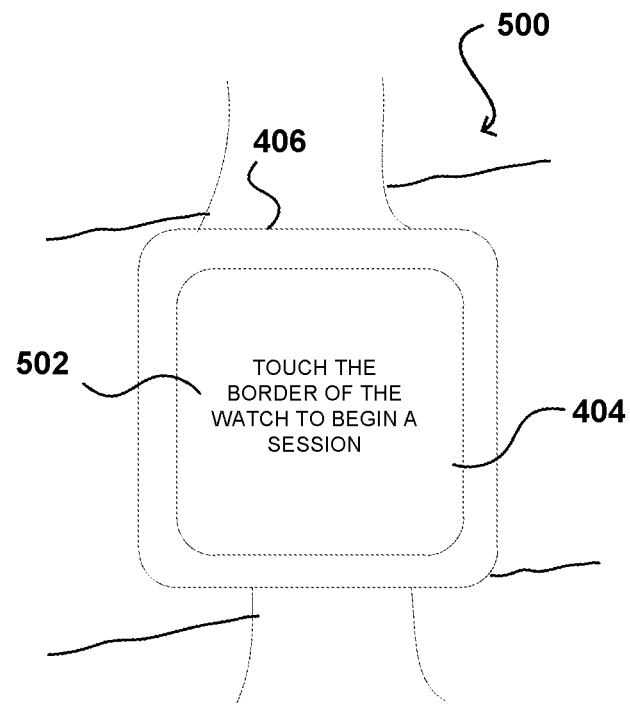
FIG. 5 illustrates an example wearable device presenting instructions to a user, in accordance with embodiments of the present disclosure.

FIG. 5 includes a representation 500 of the display 404 of the user device 406 providing a prompt 502 to the user to begin a session for recording EDA information. The prompt may be responsive to the user selecting or completing a certain mode. For example, after the user completes an exercise activity, the user device 406 may prompt the user to receive the information in order to analyze the user's response to the exercise. In various embodiments, as noted above, this could determine whether the user was particularly worn out by the exercise event, which may prompt the user to obtain additional recovery in order to maximize performance. In other embodiments, the prompt 502 may be provided before beginning an event. For example, the user may begin a meditation session and may be prompted to provide EDA information to obtain a baseline measurement of their arousal level. The user may continue to provide the information during the session in order to track their arousal levels throughout the session, which may be indicative of the user's focus or a quality of the session. For example, spikes or peaks may be indicative of distractions.

Figure 6A:
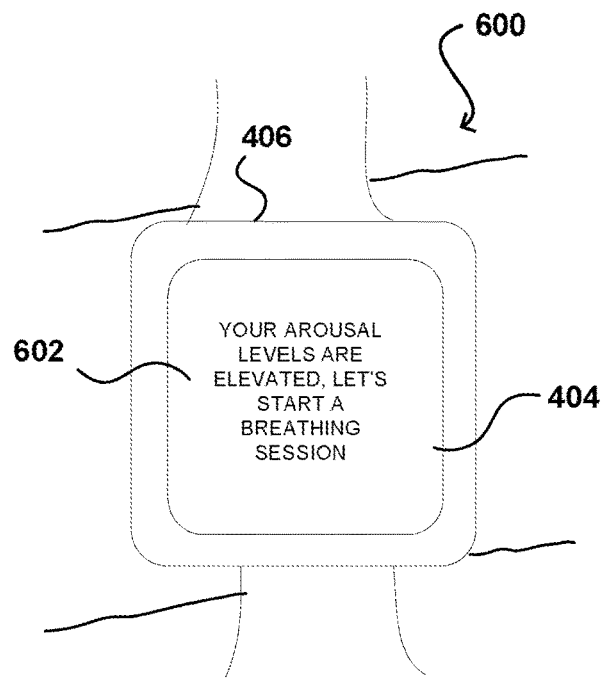
FIG. 6A illustrates an example wearable device presenting a prompt to a user, in accordance with embodiments of the present disclosure.

FIG. 6A includes a representation 600 of the display 404 of the user device 406 providing a prompt 602 to the user to begin an calming exercise after detecting an activation (e.g., arousal) that exceeds a threshold. In this embodiment, the user may have provided EDA information prior to receiving the prompt or the information may be obtained from a continuous measurement and/or from a combination of measurements received from one or more sensors. In this example, the prompt 602 recommends a breathing exercise for the user.

Figure 6B:
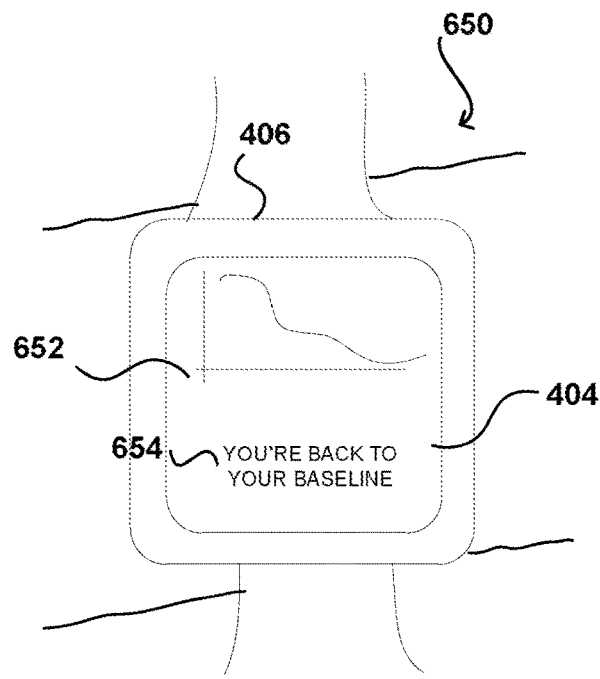
FIG. 6B illustrates an example wearable device presenting a graphical indication of arousal information, in accordance with embodiments of the present disclosure.

FIG. 6B includes a representation 650 of the display 404 of the user device 406 providing information a graphical representation 652 and message 654 to the user. The graphical representation 652 includes the EDA information in a visual format so that the user can see how his or her response decreases over time, which may be based at least in part to a guided breathing session provided by the user device 406. Additionally, the message 654 may provide information to the user throughout the session, for example, by including instructions. In this example, the user has received an affirmative message indicating that the breathing exercise has reduced their arousal levels, which may provide an incentive for the user to continue using the feature.

In various embodiments, the user device 406 may include or more features or sensors that enable detection whether or not the user has properly positioned themselves to provide the EDA information. For example, the user device 406 may include a pressure sensor that determines whether the user has sufficiently engaged the screen 404 to provide the information. Additionally, other sensors and components may also be utilized in embodiments, such as a timer to alert the user that measurements have been obtained or provide a countdown, haptic feedback to provide instructions, and the like.

Figure 7A:
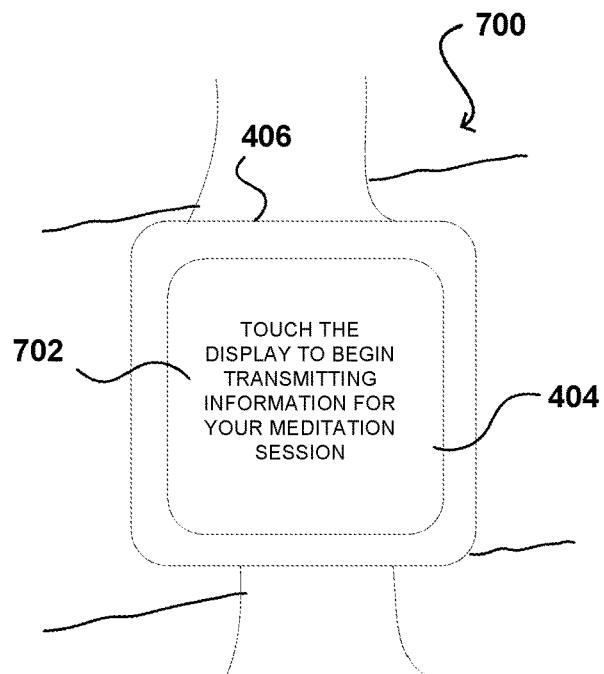
FIG. 7A illustrates an example wearable device presenting a prompt to a user, in accordance with embodiments of the present disclosure.
Figure 7B:
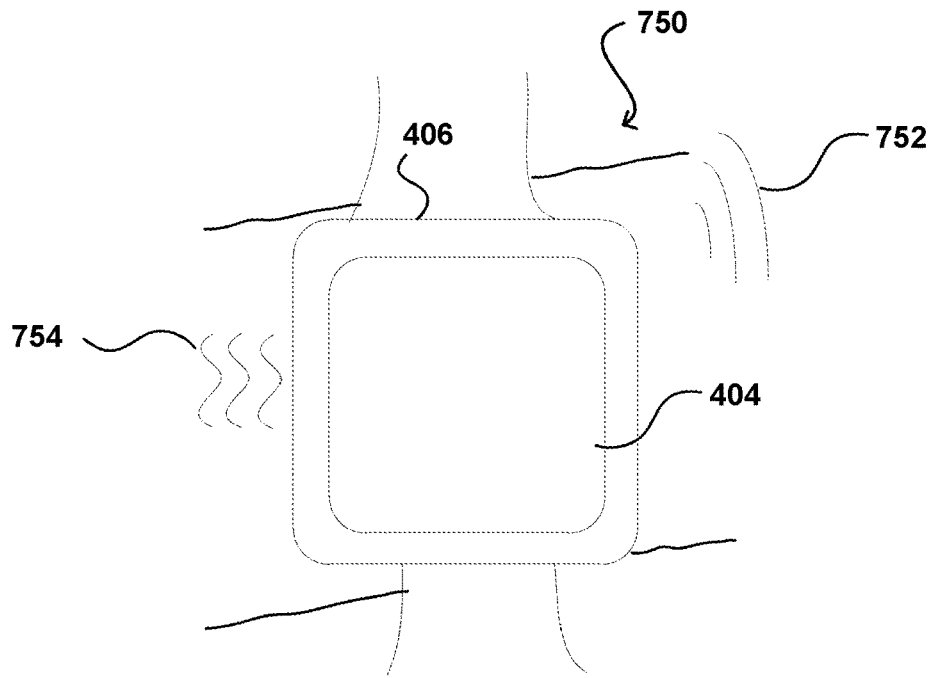
FIG. 7B illustrates an example wearable device providing feedback to a user, in accordance with embodiments of the present disclosure.

FIGS. 7A and 7B provide representations 700, 750 of a meditation session that utilizes embodiments of the present disclosure. In this example, as shown in FIG. 7A, the display 404 transmits a prompt 702 for the user to activate an EDA measurement using the user device 406. In various embodiments, the prompt 702 may be associated with a selected activity, which in this case is a meditation session. During the session, the user's arousal responses may be monitored, which may be indicative of distractions during the session. In certain embodiments, the user will maintain contact with the user device 406 during the session to provide the EDA information.

FIG. 7B includes the representation 750 in which the user device 406 provides feedback to the user in the form of an auditory sound 752 and/or vibration 754 indicative of an alert for the user regarding the elevated arousal levels. In this example, the user's EDA information may be processed to identify one or more arousal events (e.g., peaks). Upon identification, the user may be provided with feedback to make adjustments to reduce the arousal levels, thereby providing an improved medication session. It should be appreciated that messages or the like may be provided on the display 404 at this time, but it may be advantageous to black out or otherwise provide a blank screen during the meditation session.

Embodiments of the present disclosure may provide, directly within a consumer product such as a wearable, useful EDA information that users may evaluate and then respond to. For example, the user may receive an acute measurement or a continuous measurement to provide information how the user responds to certain events, such as stressful or arousing events, in order to identify steps or techniques for controlling or anticipating the response, among other benefits. Furthermore, the information may enable self-discovery for the user to monitor their arousal levels at different points in the day in order to identify triggering events or situations where arousal may spike, which may provide information to the user to make changes in their lifestyle to control these events.

Various embodiments of the present disclosure may be utilized in order to provide various levels of functionality within the wearable device described herein. By way of example, in various embodiments, the wearable device may be utilized for lie detection. For example, when an individual is nervous, he or she may exhibit a nervous system response, which may be detectable via EDA. When paired with one or more other sensors, such as a heart rate sensor, information similar that utilized in a polygraph machine may be obtained in a smaller form factor, which may provide additional use cases.

Various embodiments may also be utilized to calculate or determine a stress metric, as described in Application Ser. No. 62/062,818 filed Aug. 7, 2020. Accordingly, the EDA information may provide a piece of information to calculate additional scores or tracking information that may improve a user's day to day life or provide additional information that may facilitate improvements or changes to a user's lifestyle.

Embodiments, as noted above, may enable self-discovery for the user to identify one or more stressful or arousing events to enable a user to prepare and potentially utilize tactics to overcome the response. For example, a user may be preparing to give a speech and the anticipating may cause an arousal event detectable by the wearable device. While the user may feel confident about the speech, the information provided by the wearable may enable the user to perform one or more calming exercises prior to the speech in order to improve performance. Additionally, providing the information to the user may be indicative that the user should practice their speech again to improve their confidence.

Various embodiments may incorporate the EDA information, and potentially one or more other component of sensor information, for mental health screenings or diagnosis. As an example, a muted sensory response or an elevated sensory response may be indicative of one or more conditions, when paired with additional information that may be provided by a licensed mental healthcare practitioner. Furthermore, the EDA information may also provide information to the practitioner if the user provides consent to share that information with the practitioner, such as helping the user identify anxiety-causing events. Accordingly, the information may be utilized to detect an arousal response, which may be higher or lower than expected, in order to facilitate diagnosis.

In certain embodiments, user health and wellness may also benefit from the readings obtained by the EDA information to determine arousal responses. For example, with respect to women's health, hot flashes may be detected based on a user's response (e.g., increased sweating), which may facilitate diagnosis of the condition. In certain embodiments, a wearable may provide information to the user to predict or otherwise explain the occurrence, which may reduce the anxiety felt by the user. In the example of the hot flash, the display may provide a message informing the user they are having a hot flash, provide techniques for controlling it, and the like, which may help calm the user.

As described herein, in various embodiments cross-correlations with other sensors may also be provided and utilized. By way of example, a sleep or stress score may be improved by incorporating arousal responses, which may be indicative of disturbances during sleep and/or high stress events during the day. Additionally, other information may further be utilized to inform or improve the detection and classification of arousal events. For example, heart rate, heart rate variation, respiratory rate, and the like may be indicators of an arousal event. However, as noted above, the additional information may also be used to disregard an arousal event, such as an elevated response during known strenuous exercise. In this manner, the arousal responses may have their thresholds and/or baselines adjusted based on information from the other sensors. Additionally, various sensors and sensor information may provide information to the sensor to begin recording data. For example, an accelerometer within the wearable may indicate that the user is not sitting still, which may lead to noisy or unreliable information.

Embodiments of the present disclosure may also be particularly selected to perform high frequency measurements (e.g., approximately 125 Hz), compared to traditional techniques that utilized lower frequencies. As a result, existing on board power supplies and systems may be utilized, which decreases the weight and complexity of the circuit design for the wearable. For example, in various embodiments, high frequency measurements may provide reduced quality signals, however, the presence of the other components of the wearable device may drive design of the circuitry for conducting EDA measurements. Various embodiments may include one or more switching circuits to improve data acquisition and/or increase a current intensity in order to improve signal quality.

Figure 8:
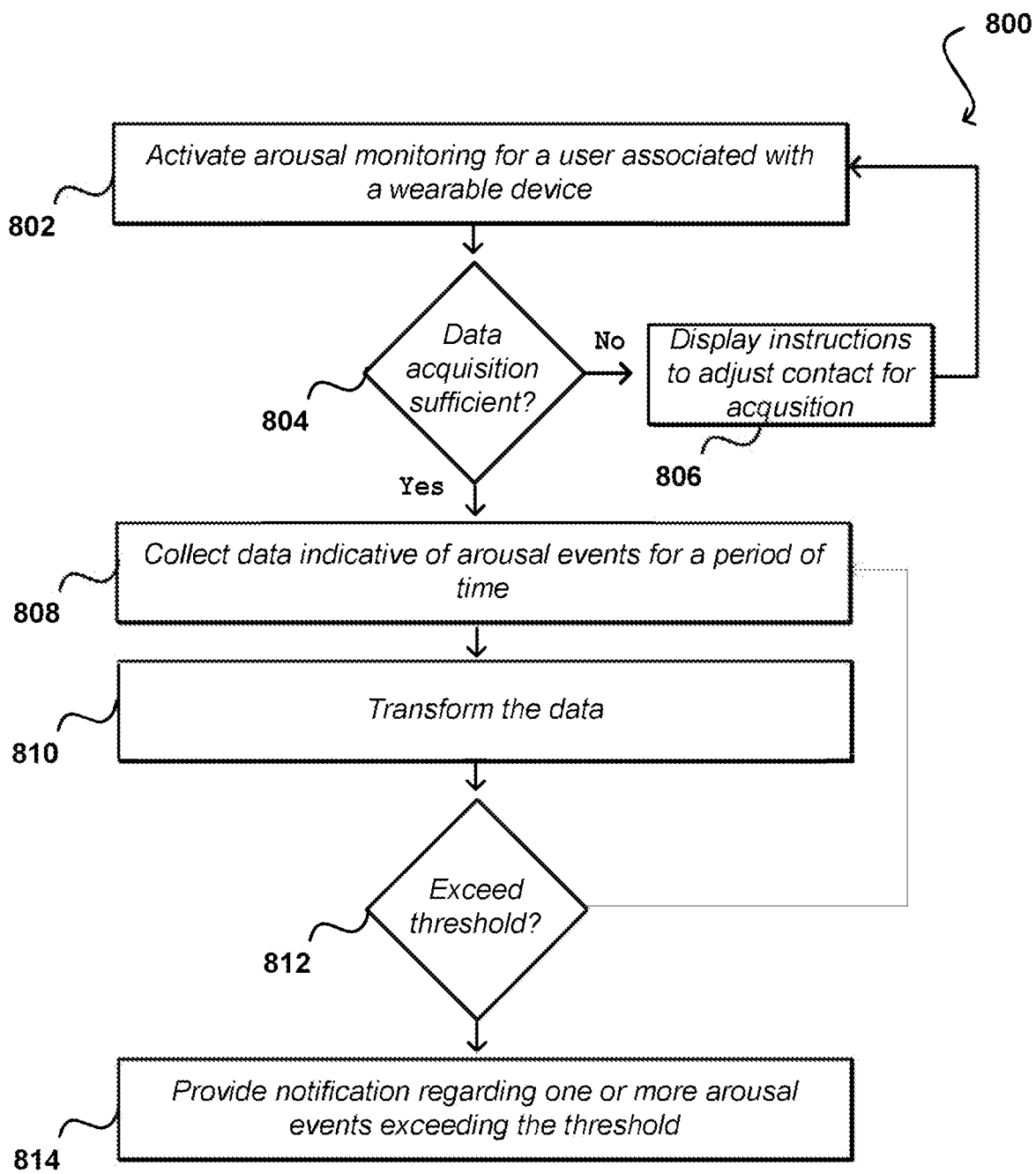
FIG. 8 illustrates an example process for determining an arousal event, in accordance with embodiments of the present disclosure.

Referring now to FIG. 8, a flow chart of an embodiment of a method 800 for identifying an arousal event according to the present disclosure is illustrated. It should be understood that, for any process discussed herein, there can be additional, fewer, or alternative steps performed in similar or alternative orders, or in parallel, within the scope of the various embodiments. In this example, as shown at (802), the method 800 includes activating an arousal monitoring service for a user device. For example, the user may load a program stored on the wearable device that receives sensor information to evaluate or determine a user's arousal levels responsive to events in their life. As shown at (804), the method 800 includes evaluating whether data acquisition is sufficient, such as the user having a proper connection with a lead or electrode. If not, as shown at (806), the method 800 includes displaying instructions for the user to adjust contact for acquisition. If yes, as shown at (808), the method 800 includes collecting data indicative of arousal events for a period of time. In various embodiments, the data collection may be EDA information that may be utilized to determine arousal events, which may be indicated by an increased skin conductivity. As shown at (810), the method 800 includes transforming the data, for example, by evaluating the information continuously for a given time period and/or over certain periods of time and then averaged or normalized to enable smoothing of the data. Additional transformations may be applied to the data, such as changing a format to enable interaction with one or more other devices. In certain embodiments, the transformation is a derivative.

As shown at (812), the method 800 includes evaluating the data to determine whether one or more segments or bins exceeds a threshold. For example, the threshold may be a minimum threshold value that is indicative of an arousal event. Additionally, the threshold may be a percentage increase over a calculated baseline event for the user. Various other methods may also be utilized to identify the threshold. For example, the threshold may be related to a sudden change that exceeds a certain percentage of the data for a time period preceding it. Additionally, the threshold may also be evaluate din terms of how many different peaks or changes there are over a period of time. Thereafter, as shown at (814), the method 800 includes providing a notification to the user regarding the arousal event. For example, the user may be informed of the arousal event and provided with a suggestion to perform one or more exercises to relax.

Figure 9:
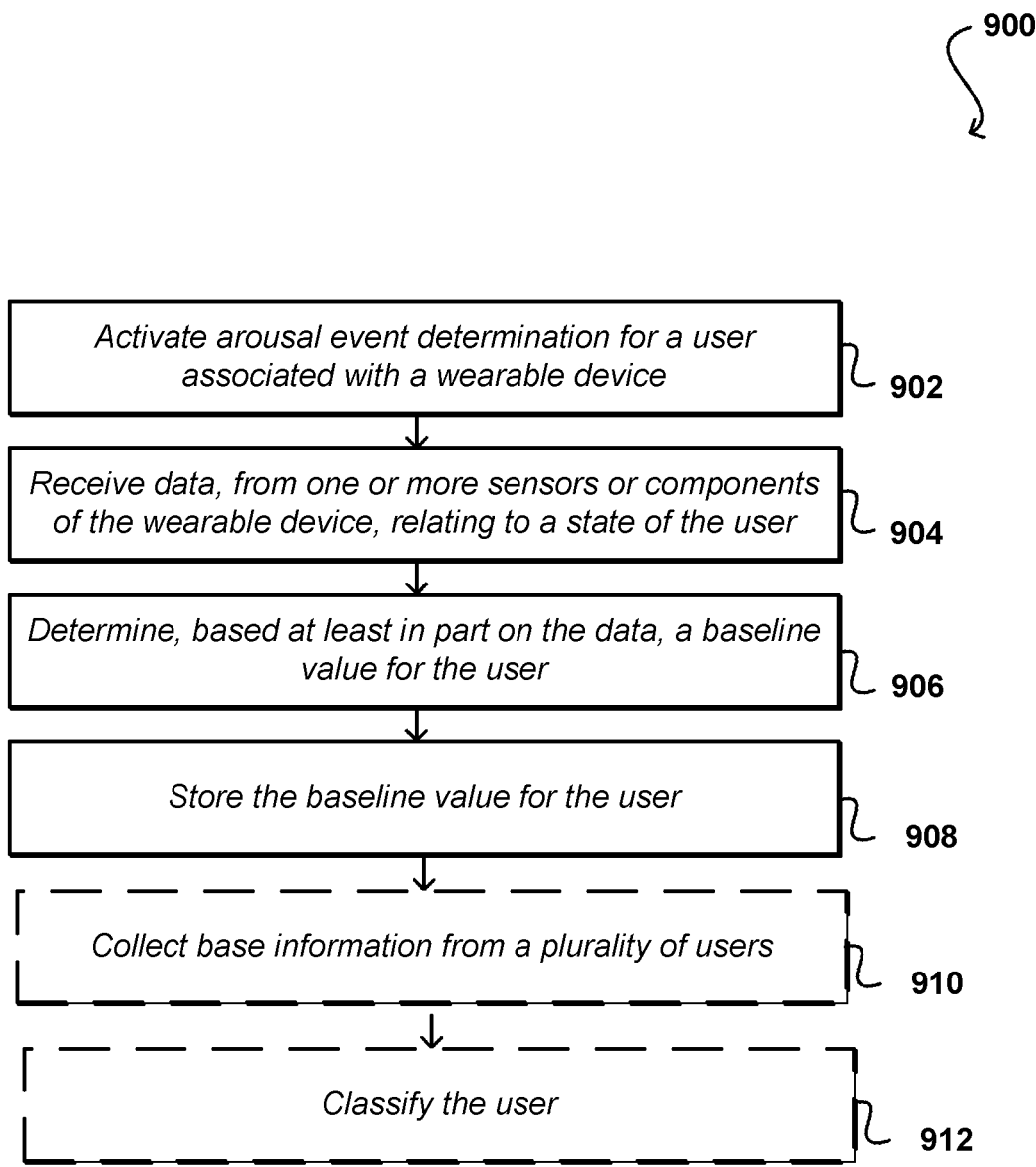
FIG. 9 illustrates an example process for determining a baseline arousal level, in accordance with embodiments of the present disclosure.

FIG. 9 is a flow chart of an embodiment of a method 900 for determining a baseline level for a user according to the present disclosure. The baseline level for the user may refer to a baseline EDA response and/or baseline arousal level. The baseline may correspond to a value of the response and/or a number of response elevations over a period of time. In this example, as shown at (902), the method 900 includes activating an arousal event determination for a user associated with a wearable device 902. For example, the user may selectively load an application that records EDA information to determine an arousal level. As shown at (904), the method 900 includes receiving data from one or more sensors of the wearable device. The data may be correlated to a state, such as "not aroused" and "aroused." As shown at (906), the method 900 includes determining, based at least in part on the data, a baseline value for the user. In various embodiments, the user may receive instructions for providing the information to determine the baseline. For example, the user may be instructed to sit quietly for a short period of time prior to providing the information. The baseline, as described above, may be correlated to a response level or to a number of elevated responses over a period of it. In various embodiments, the baseline may be updated over time. For example, an average arousal may be determined over different periods of the day and then averaged to generate a baseline arousal. In this manner, the user's baseline may be adjusted over time to accommodate different events or changes in the user's life. As shown at (908), the method 900 includes storing the baseline value for the user. In certain embodiments, different values may be stored for different activities, such as a baseline for working, a baseline for exercising, etc. In certain embodiments, as shown at (910), the method 900 may include collecting base information from a plurality of other users, e.g., who have provided permission to have their information collected and anonymized. As shown at (912), the method 900 may include classifying the user. For example, the classifications may be based on a user's demographic information, location, job, or the like. In this manner, an initial baseline may be provided and then the user's information may be adjusted from the baseline that may be predicted based on other similar users.

Figure 10:
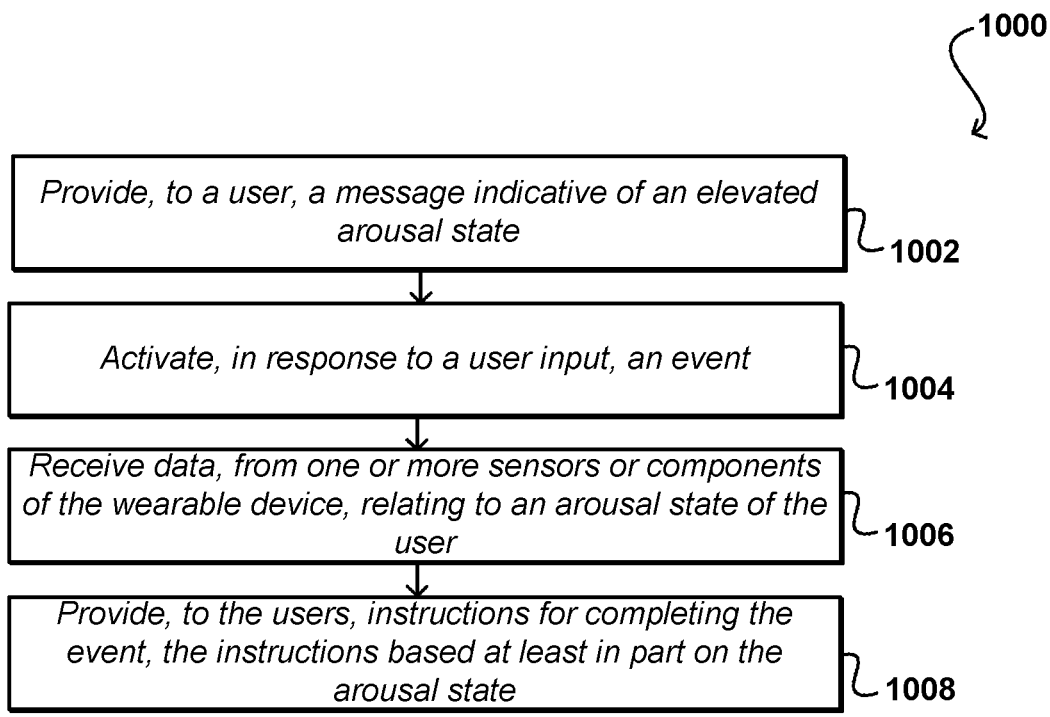
FIG. 10 illustrates an example process for guiding a user through an event, in accordance with embodiments of the present disclosure.

FIG. 10 is a flow chart of an embodiment of a method 1000 for providing instructions to a user to complete an event responsive to user's arousal state. In this example, a message is provided to a user indicative of an elevated arousal state 1002. For example, a wearable device may provide a message or alert indicative of a detected elevated arousal state, which may be obtained from EDA information acquired via the device. The user may provide an input requesting participation in an event 1004. By way of example, the event may be a guided meditation application that provides the user with breathing exercises that may be particularly selected to reduce the user's present elevated arousal state. Information may be received related to an arousal state of the user 1006. For example, the user may be instructed to position a portion of their body on the wearable to enable data collection. The device may then provide instructions for completing the event 1008. In the example of a guided meditation application, the instructions may relate to breathing exercises. During the event, the user's information and arousal state may be monitored. In various embodiments, the event may be a timed event or the event may continue until the user's arousal state reaches a determined level. In this manner, a user in a heightened state of arousal may be notified and then instructed to take action to reduce their arousal state.

Figure 11:
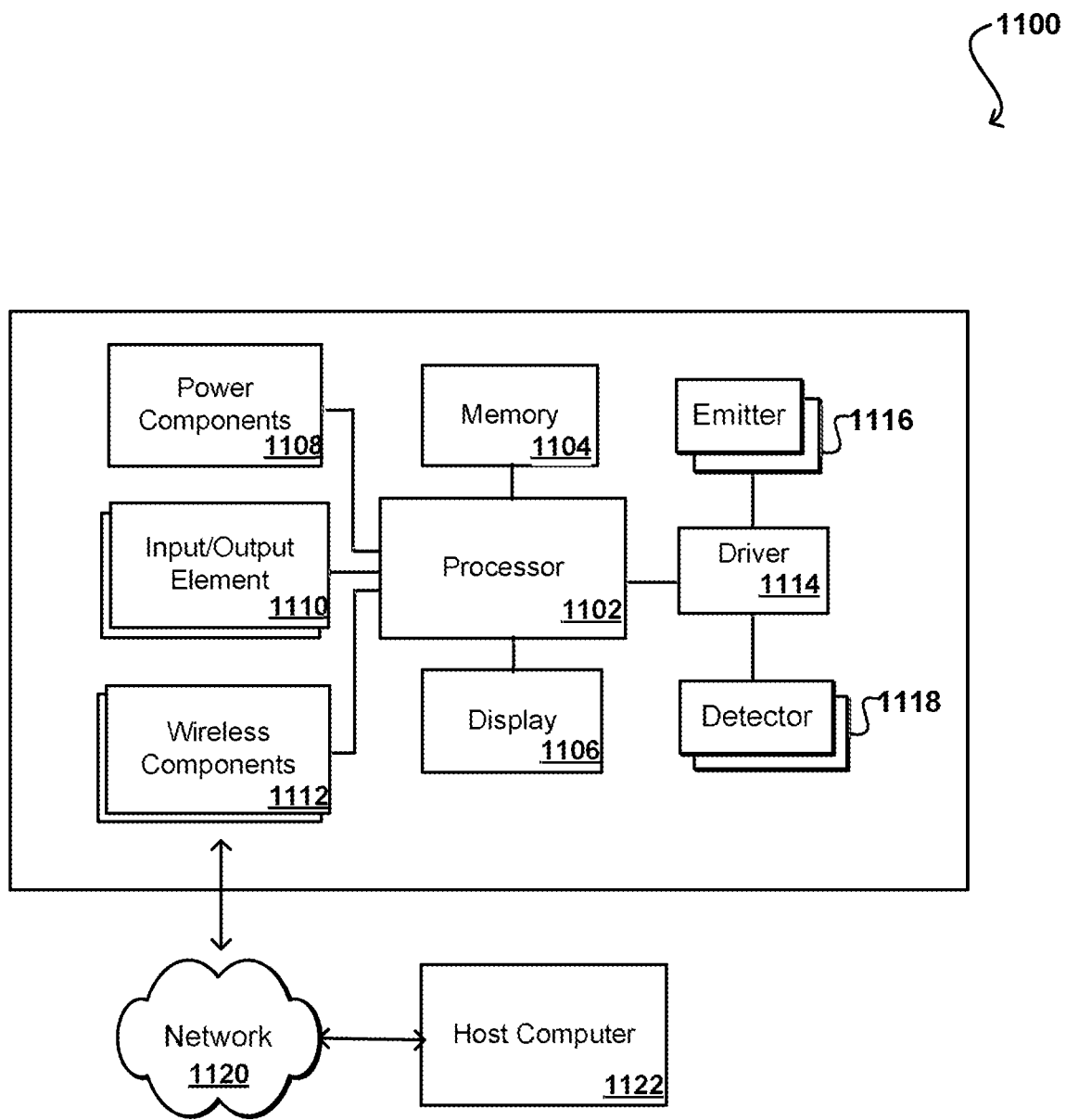
FIG. 11 illustrates a set of basic components of one or more devices of the present disclosure, in accordance with various embodiments of the present disclosure.

FIG. 11 illustrates a set of basic components 1100 of one or more devices according to the present disclosure, in accordance with various embodiments of the present disclosure. In this example, the components 1100 include at least one processor 1102 for executing instructions that can be stored in a memory device or element 1104. As would be apparent to one of ordinary skill in the art, the device can include many types of memory, data storage or computer-readable media, such as a first data storage for program instructions for execution by the processor(s) 1102, the same or separate storage can be used for images or data, a removable memory can be available for sharing information with other devices, and any number of communication approaches can be available for sharing with other devices. The components 1100 also include at least one type of display 1106, such as a touch screen, electronic ink (e-ink), organic light emitting diode (OLED) or liquid crystal display (LCD), although devices such as servers might convey information via other means, such as through a system of lights and data transmissions. Further, the components 1100 include one or more networking device 1108, such as a port, network interface card, or wireless transceiver that enables communication over at least one network. Moreover, as shown, the components 1100 include at least one input/output element 1110 able to receive conventional input from a user. The input/output element 1110 can include, for example, a push button, touch pad, touch screen, wheel, joystick, keyboard, mouse, trackball, keypad or any other such device or element whereby a user can input a command to the device. Further, the input/output element(s) 1110 may also be connected by a wireless infrared or Bluetooth or other link as well in some embodiments. In some embodiments, however, such a device might not include any buttons at all and might be controlled only through a combination of visual and audio commands such that a user can control the device without having to be in contact with the device.

As discussed, different approaches can be implemented in various environments in accordance with the described embodiments. As will be appreciated, although a Web-based environment is used for purposes of explanation in several examples presented herein, different environments may be used, as appropriate, to implement various embodiments. The components 1100 may also include an electronic client device, which can include any appropriate device operable to send and receive requests, messages or information over an appropriate network and convey information back to a user of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server for receiving requests and serving content in response thereto, although for other networks, an alternative device serving a similar purpose could be used, as would be apparent to one of ordinary skill in the art.

The illustrative environment includes at least one application server and a data store. It should be understood that there can be several application servers, layers or other elements, processes or components, which may be chained or otherwise configured, which can interact to perform tasks such as obtaining data from an appropriate data store. As used herein, the term "data store" refers to any device or combination of devices capable of storing, accessing and retrieving data, which may include any combination and number of data servers, databases, data storage devices and data storage media, in any standard, distributed or clustered environment. The application server can include any appropriate hardware and software for integrating with the data store as needed to execute aspects of one or more applications for the client device and handling a majority of the data access and business logic for an application.

The application server provides access control services in cooperation with the data store and is able to generate content such as text, graphics, audio and/or video to be transferred to the user, which may be served to the user by the Web server in the form of HTML, XML or another appropriate structured language in this example. The handling of all requests and responses, as well as the delivery of content between the client device and the application server, can be handled by the Web server. It should be understood that the Web and application servers are not required and are merely example components, as structured code discussed herein can be executed on any appropriate device or host machine as discussed elsewhere herein. The data store can include several separate data tables, databases or other data storage mechanisms and media for storing data relating to a particular aspect. For example, the data store illustrated includes mechanisms for storing content (e.g., production data) and user information, which can be used to serve content for the production side. The data store is also shown to include a mechanism for storing log or session data. It should be understood that there can be many other aspects that may need to be stored in the data store, such as page image information and access rights information, which can be stored in any of the above listed mechanisms as appropriate or in additional mechanisms in the data store. The data store is operable, through logic associated therewith, to receive instructions from the application server and obtain, update, or otherwise process data in response thereto. In one example, a user might submit a search request for a certain type of item. In this case, the data store might access the user information to verify the identity of the user and can access the catalog detail information to obtain information about items of that type. The information can then be returned to the user, such as in a results listing on a Web page that the user is able to view via a browser on the user device. Information for a particular item of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated. Thus, the depiction of the systems herein should be taken as being illustrative in nature and not limiting to the scope of the disclosure.

The various embodiments can be further implemented in a wide variety of operating environments, which in some cases can include one or more user computers or computing devices which can be used to operate any of a number of applications. User or client devices can include any of a number of general purpose personal computers, such as desktop or notebook computers running a standard operating system, as well as cellular, wireless, and handheld devices running mobile software and capable of supporting a number of networking and messaging protocols. Devices capable of generating events or requests can also include wearable computers (e.g., smart watches or glasses), VR headsets, Internet of Things (IoT) devices, voice command recognition systems, and the like. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network and any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving, and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In certain embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer, or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus, the breadth and scope of the present disclosure should not be limited by any of the above-described exemplary embodiments.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a"

or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Figure 12:
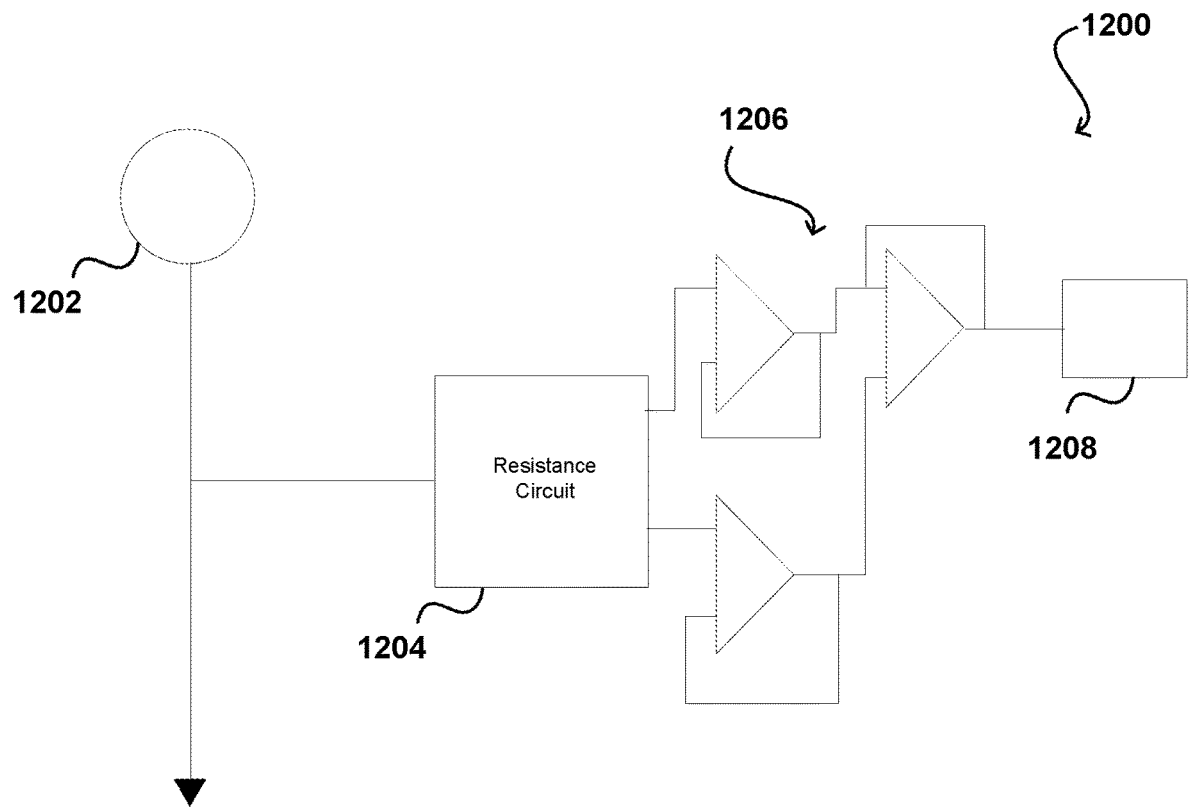
FIG. 12 illustrates an example circuit arrangement for measuring electrodermal activity (EDA), in accordance with various embodiments of the present disclosure.

Referring now to FIG. 12, a schematic diagram of one embodiment of a circuit 1200 for conducting EDA measurements according to the present disclosure is illustrated. It should be appreciated that the circuit 1200 is provided for illustrative purposes only and in various embodiments different configurations may be used. Additionally, various features have been omitted for clarity, such as resistors and ground connections. As shown, the illustrated circuit 1200 includes a power supply 1202, which may be provided by a battery of a wearable device. As will be appreciated, the power supply may be a DC power supply and may also provide electrical energy to other components within the wearable device, and as a result, operation of the circuit 1200 may be regulated by how the power supply 1202 interacts with various other components of the wearable device. The circuit 1200 may further include a resistance circuit 1204 that receives power from the power supply 1202 to measure skin conductance, as an example. In various embodiments, the resistance circuit 1204 may include one or more electrodes that the user may contact, for example, with the user's fingers, with the user's palm and wrist, and/or any combination, as described herein. Accordingly, the resultant resistance is provided as input to various operational amplifiers (op amps) 1206 to provide an increased output potential. An output circuit 1208 may receive the information from the series of op amps 1208 and may, in various embodiments, transmit the output to one or more controllers for further computation.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A method for utilizing a wrist-worn wearable computing device to detect an arousal event of a user, comprising:
   receiving, from a plurality of sensors on the wrist-worn wearable computing device, data indicative of the arousal event, the plurality of sensors comprising a first electrode on a bottom face of the wrist-worn wearable computing device and contacting a wrist of the user and a second electrode on a top surface of the wrist-worn wearable computing device, the first and second electrodes being electrically isolated within the wrist-worn wearable computing device, wherein the data indicative of the arousal event comprises, at least, electrodermal activity (EDA) data captured when the user places one or more fingers on the second electrode on the top surface of the wrist-worn wearable computing device, the second electrode comprising at least one EDA sensor that measures, at least, a skin conductance response to sweat or moisture on the skin of the user;
   comparing the EDA data to a threshold; and
   displaying, via a display screen of the wearable computing device, a notification to the user identifying the arousal event based on the comparison.

2. The method of claim 1, wherein the arousal event is caused by a sympathetic nervous system response of the user.

3. The method of claim 2, wherein the notification comprises a recommendation for the user as to how to lower the sympathetic nervous system response.

4. The method of claim 1, wherein the data indicative of the arousal event comprises electrocardiography (ECG) data captured using the plurality of sensors, the plurality of sensors comprising at least one ECG sensor.

5. The method of claim 1, further comprising transforming the data indicative of the arousal event.

6. The method of claim 5, wherein transforming the data indicative of the arousal event comprises at least one of computing a derivative of the data, averaging the data over a plurality of bins, normalizing the data, or filtering the data.

7. The method of claim 1, further comprising:
   activating, upon receiving an input from the user, an arousal monitoring service;
   providing, to the user, instructions to data acquisition; and
   determining user contact with the wrist-worn wearable computing device for the data acquisition is sufficient.

8. A wrist-worn wearable computing device, comprising:
   a housing;
   a display screen on the housing;
   a plurality of sensors, the plurality of sensors comprising a first electrode on a bottom face of the housing positioned to contact a wrist of a user and a second electrode on a top surface of the wrist-worn wearable computing device, the first and second electrodes being electrically isolated within the housing, the second electrode comprising at least one EDA sensor that measures a skin conductance response to sweat or moisture on skin of the user;
   at least one processor; and
   memory including instructions that, when executed by the at least one processor, cause the at least one processor to:
      receive, from the plurality of sensors, data indicative of an arousal event, wherein the data indicative of the arousal event comprises electrodermal activity (EDA) data captured from finger contact on the second electrode;
      compare the EDA data to a threshold; and
      display, via the display screen, a notification to the user identifying the arousal event based on the comparison.

9. The wrist-worn wearable computing device of claim 8, wherein the arousal event is caused by a sympathetic nervous system response of the user, and wherein the notification comprises a recommendation for the user as to how to lower the sympathetic nervous system response.

10. The wrist-worn wearable computing device of claim 8, wherein the plurality of sensors further comprise one or more electrocardiography (ECG) sensors, wherein the data indicative of the arousal event comprises the EDA data and ECG data from the one or more ECG sensors.

11. The wrist-worn wearable computing device of claim 8, wherein the instructions, when executed by the least one processor, further cause the at least one processor to:
   transform the data indicative of the arousal event.

12. The wrist-worn wearable computing device of claim 11, wherein transforming the data indicative of the arousal event comprises at least one of computing a derivative of the data, averaging the data over the plurality of bins, normalizing the data, or filtering the data.

13. The wrist-worn wearable computing device of claim 8, wherein the instructions, when executed by the least one processor, further cause the at least one processor to:
   activate, upon receiving an input from the user, an arousal monitoring service;
   provide, to the user, instructions to data acquisition; and
   determine user contact with the wrist-worn wearable computing device for the data acquisition is sufficient.

14. A non-transitory computer-readable storage medium comprising instructions that, when executed by at least one processor, cause the at least one processor to:
   receive, from a plurality of sensors on a wearable computing device, data indicative of an arousal event, the plurality of sensors comprising a first electrode on a bottom face of the wrist-worn wearable computing device and a second electrode on a top surface of the wrist-worn wearable computing device, the first and second electrodes being electrically isolated within the wrist-worn wearable computing device, wherein the data indicative of the arousal event comprises, at least, electrodermal activity (EDA) data captured by the second electrode on the top surface of the wrist-worn wearable computing device, the second electrode comprising at least one EDA sensor that measures, at least, a skin conductance response to sweat or moisture;
   compare the EDA data to a threshold; and
   display, via the display screen, a notification to a user identifying the arousal event based on the comparison.

15. The non-transitory computer-readable storage medium of claim 14, wherein the plurality of sensors further comprise one or more electrocardiography (ECG) sensors, wherein the data indicative of the arousal event comprises the EDA data and ECG data from the one or more ECG sensors.

16. The non-transitory computer-readable storage medium of claim 14, wherein the instructions, when executed by at least one processor, further cause the at least one processor to:
   activate, upon receiving an input from the user, an arousal monitoring service;
   provide, to the user, instructions to data acquisition; and
   determine user contact with the wrist-worn wearable computing device for the data acquisition is sufficient.

* * * * *